United States Patent [19]

Dröge et al.

[11] Patent Number: 5,607,974
[45] Date of Patent: Mar. 4, 1997

[54] TREATMENT OF DISEASES ASSOCIATED WITH CYSTEINE DEFICIENCY

[75] Inventors: Wulf Dröge, Heidelberg, Germany; Leonard A. Herzenberg; Leonore A. Herzenberg, both of Stanford, Calif.

[73] Assignees: The Board of Trustees of the Leland Stanford Junior University, Palo Alto, Calif.; Deutsches Krebsforschungszentrum, Germany

[21] Appl. No.: 180,778

[22] Filed: Jan. 10, 1994

Related U.S. Application Data

[63] Continuation of Ser. No. 913,752, Jul. 17, 1992, abandoned, which is a continuation of Ser. No. 302,396, Jan. 26, 1989, abandoned.

[51] Int. Cl.$^6$ ..................... A61K 31/195; A61K 31/70
[52] U.S. Cl. ................................ 514/562; 514/49
[58] Field of Search .................... 514/562, 2, 49

[56] References Cited

U.S. PATENT DOCUMENTS

| 4,148,885 | 4/1979 | Renoux | 424/162 |
|---|---|---|---|
| 4,335,210 | 6/1982 | Meister et al. | 435/113 |
| 4,434,158 | 2/1984 | Meister et al. | 424/94 |
| 4,438,124 | 3/1984 | Meister et al. | 424/270 |
| 4,440,788 | 4/1984 | Tgrayama et al. | 514/893 |
| 4,647,571 | 3/1987 | Meister et al. | 514/369 |
| 4,665,082 | 5/1987 | Meister et al. | 514/365 |
| 4,710,489 | 12/1987 | Meister | 514/18 |
| 4,744,989 | 5/1988 | Payne et al. | 424/493 |
| 4,758,551 | 7/1988 | Meister et al. | 514/18 |
| 4,772,471 | 9/1988 | Vanlerberghe et al. | 424/450 |
| 4,784,685 | 11/1988 | Meister | 71/106 |
| 4,789,633 | 12/1988 | Huang et al. | 424/417 |
| 4,879,370 | 11/1989 | Meister | 530/331 |

FOREIGN PATENT DOCUMENTS

| 0158487 | 3/1985 | European Pat. Off. . |
| 3812008 | 4/1988 | Germany . |
| 3707127 | 9/1988 | Germany . |
| WO8809674 | 6/1988 | WIPO . |

OTHER PUBLICATIONS

Super Nutrition by Richard Passwater, 1976 pp. 154, 155 Gulfwestern Pocket Books, NY. NY.
Human Nutrition Burton et al. 4th Ed. 1988 McGraw Hill pp. 50–53, 60–62.
Droge et al. Biol. Chem. Hoppe–Seyler 369:143–148–1988.
Miester et al. Seminars in Oncology, vol. 10/1/supp. 1 Mar. 1983.
West et al.: Textbook of Biochemistry Fourth Edition. pp. 1143–1147; 1243–1250.
Kinter et al, Trans. Assoc. Am. Physicians, vol. 105, p. 36 (1992).
Eylar et al, International Immunology, vol. 5, pp. 97–101 (1993).

Dröge, et al. "Abnormal Amino–Acid Concentrations in the Blood of Patients with Acquired Immunodeficiency Syndrome (AIDS) May Contribute to the Immunological Defect", Biol. Chem. Hoppe–Seyler (1988) 369:143–148.
Miller and Rumack "Clinical Safety of High Oral Doses of Acetylcysteine" Seminars in Ocology (1983, Suppl. 1, Mar.) vol. 10.
Ohmori and Yamamoto, "Mechanism of Augmentation of the Antibody Response in vitro by 2–Mercaptoethanol in Murine Lymphocytes", J. Exp. Med. (1982) 155:1277–1290.
Ishii T, Sugita Y, Bannai S. Regulation of glutathione levels in mouse spleen lymphocytes by transport of cysteine. J Cell Physiol 133:330–336, 1987.
Eck H, Gmunder H, Hartmann M, Petzoldt D, Daniel V, Droge W. Low concentrations of acid–soluble thiol (cysteine) in the blood plasma of HIV–1–infected patients. Biol Chem Hoppe–Seyler 370: 101–108, 1989.
Eck H, Droge W. Influence of the extracellular glutamate concentration on the intracellular cyst(e)ine concentration in macrophages and on the capacity to release cysteine. Biol Chem Hoppe–Seyler 370: 109–113, 1989.
Fidelus R K, Tsan M. Enhancement of intracellular glutathione promotes lymphocyte activation by mitogen. Cell Immunol 97: 155–163, 1986.
Kosower E M, Kosower N S. Lest I forget thee, glutathione. Nature 224: 117–120, 1969.
Ketterer B. Protective role of glutathione and glutathione transferases in mutagenesis and carcinogenesis. Mutation Res 202: 343–361, 1988.
Ziegler D M. Role of reversible oxidation–reduction of enzyme thiols–disulfides in metabolic regulation. Annu Rev Biochem 54: 305–329, 1985.
Orrenius S, Jewell S A, Bellomo G, et al. Regulation of calcium compartmentation in the hepatocyte—a critical role of glutathione. In "Functions of Glutathione": Raven Press. New York. pp. 261–271. 1983.
Martensson J, Meister J. Mitochondrial damage in muscle occurs after marked depletion of glutathione and is prevented by giving glutathione monoester. Proc Natl Acad Science USA 86: 471–475, 1989.
Droge W, Pottmeyer–Gerber C, Schmidt H, Nick S. Glutathione augments the activation of cytotoxic T lymphocytes in vivo. Immunobiol 172: 151–156, 1986.
Ristow S S, Starkey J R, Stanford D R, et al. Cell surface thiols, but not intracellular glutathione, are essential for cytolysis by a cloned murine natural killer cell line. Immunol Invest 14: 401–414, 1985.

(List continued on next page.)

Primary Examiner—Neil Levy
Attorney, Agent, or Firm—Bertram I. Rowland; Flehr, Hohbach, Test, Albritton & Herbert

[57] ABSTRACT

Patients suffering from a pathological condition resulting in reduced intracellular cysteine levels are treated with a cysteine source capable of being transported to the cellular cytoplasm. Particularly, N-acetyl cysteine is employed in the treatment of AIDS patients.

3 Claims, No Drawings

OTHER PUBLICATIONS

Bannai S, Tateishi N. Role of membrane transport in metabolism and function of glutathione in mammals. J Membr Biol 89: 1–8, 1986.

Meister A, Anderson M E, Hwang O. Intracellular cysteine and glutathione delivery systems. J Am Coll Nutr 5: 137–151, 1986.

Richman D D, Andrews J, and AZT Collaborative Working Group. Results of continued monitoring of participants in the placebo–controlled trial of zidovudine for serious human immunodeficiency virus infection. Am J Med 85 (suppl 2A): 208–213, 1988.

Moldeus P, Cotgreave I A, Berggren M. Lung protection by a thiol–containing antioxidant: N–acetylcysteine. Respiration 50(Suppl 1): 31–42, 1986.

Ziment I, Acetylcysteine: A Drug with an Interesting Past and a Fascinating Future, Respiration 50(Suppl 1) 26–30 (1986).

Yunis A, DNA Damage Induced by Chloramphenicol and Nitroso–Chloramphenicol: Protection by N–Acetylcysteine Respiration 50(Suppl 1) pp. 50–55 (1986).

DeJong et al. Jour of Immunological Methods, 68 (1984) 55–60.

TREATMENT OF DISEASES ASSOCIATED WITH CYSTEINE DEFICIENCY

This application is a continuation of application Ser. No. 07/913,752, filed on Jul. 17, 1992, which was a Continuation of application Ser. No. 07/302,396, filed on Jan. 26, 1989, both now abandoned.

INTRODUCTION

1. Technical Field

The subject field concerns disease treatment associated with intracellular cysteine deficiency.

2. Background

For many diseases there are no present cures. For the most part, treatment may be associated with various palliatives, so as to mitigate the suffering and disability during the course of the disease. One of these diseases is AIDS, which when it reaches full blown AIDS is fatal. While the retroviral cause of the disease is not mortal to the host, the virus so debilitates the immune system, as to make the patient susceptible to opportunistic diseases. Therefore, most victims succumb to diseases such as Kaposi's sarcoma, pneumonia, or other opportunistic pathogen. During the course of the disease which can extend over years, the patient is severely debilitated, unable to work or fill simple domestic functions. It is therefore of great interest in the case of AIDS and other diseases to at least treat or ameliorate the symptoms, so as to diminish the debilitating effects of the disease and potentially prolong the life of the patient.

Relevant Literature

Dröoge et al., Biol. Chem. Hoppe-Seyler 369, 143–148(1988) report a reduction in cystine and methionine in AIDS patients, with an elevated concentration of arginine and glutamate, where mitosis is indicated as being inhibited by extracellular glutamate and augmented by cystine. Miller and Rumack, Seminars in Oncology, 10 Suppl. 1, 76–85 describe the effect of N-acetyl cysteine in the treatment of acetaminophen overdose. Resulting mitogenic responses and the augmented production of antibody in lymphocyte cultures by unphysiologically high concentrations of cystine or cysteine have been previously reported. For example, Ohmori and Yamamoto, J. Exp. Med. 155, 1277–1290 (1982) De Jong and Van der Meer, J. Immunol. Methods 68, 55–60(1984); and Ishii et al., Cell. Physiol. 133, 330–336(1987) report that murine lymphocytes have weak transport activity for cystine and strong transport activity for cysteine.

SUMMARY OF THE INVENTION

Compositions and methods are provided for the treatment of mammalian, particularly human, patients who as a result of a diseased state have intracellular cysteine deficiency. Particularly, cysteine in a form for intracellular transport is administered to the patient in an amount sufficient to supplement intracellular cysteine deficiency. The cysteine source may be administered by itself or in conjunction with other drugs suitable for the amelioration or treatment of the disease.

DESCRIPTION OF THE SPECIFIC EMBODIMENTS

Methods and composition are provided for treatment of a diseased, stressed, or pathological mammalian, usually human, patient, as a result of a pathogen, neoplasia, hemodialysis, apheresis, genetic condition, exposure to toxic agent, old age, excessive exercise, or the like, which results in a cysteine deficiency in the cells of the host, particularly in hematopoietic cells. The lack of intracellular cysteine may be associated with an extracellular enhancement and concentration of glutamate. Furthermore, the cysteine deficiency may be associated with a failure of cystine transport.

The subject method finds particular application with HIV induced diseases, such as lymphadenopathy syndrome, AIDS related complex, AIDS, and other diseases, particularly of retroviral etiology. Other diseases include acquired and inherited hemolytic diseases, other immune deficiencies, hematopoietic system deficiencies, renal failure, diseases associated with plasmapheresis, hemodialysis, neurological effects of cysteine or glutathione deficiencies, Alzheimer's disease, other diseases of senility or old age, e.g., loss of memory, diseases as a result of exchanges of small molecules from blood, neurotoxicity from elevated glutamate, various solid organ diseases, e.g., lung, kidney, pancreas, muscle, heart, etc., as a result of elevated glutamate or cysteine/glutathione deficiencies, etc. The cysteine source may also be used as a preventative or prophylactically in combination with such drugs as acetaminophen.

The treatment of the patient may be with any drug which can be transported into the cytoplasm of the cell and/or elevate plasma thiol levels and which provide cysteine or derivatives thereof, e.g., glutathione, where the effect is to counter the cysteine/glutathione deficiency to the cell. Thus, normally cysteine derivatives will be employed which are physiologically acceptable, are transportable across the cellular membrane, and, as appropriate, may serve as a cysteine source. These drugs include N-acetyl cysteine, thiazolidine derivatives (e.g., pyruvyl-cysteine), glutamylcysteine, N-formyl cysteine, or other physiologically acceptable acyl (1–7 carbon atoms) or keto-carbonyl derivatives.

Instead of drugs which are transportable across the membrane, liposomes may be employed, where cysteine or an acceptable derivative, may be present in the lumen of the liposome. Preparation of liposomes is conventional and is extensively described in the literature, and need not be described here. The concentration of the cysteine or cysteine derivative in the liposome lumen will generally be in the range of about 50 µg/ml to 5 mg/ml. The particle size of the liposomes will generally be in the range of about 1 to 500 microns. Of particular interest for those diseases where the infection is associated with specific cells, the liposomes may be bound to molecules which provide for specific targeting. For example, antibodies may be bound to the liposome, either covalently or non-covalently, where the antibodies may be specific for CD3, -4, -8, Mac-1, or combinations thereof, or the like.

The cysteine source, by itself or in combination with other drugs, may be formulated in a variety of ways, such as powders, liquids, tablets, slow-release particles, etc. The formulations may include conventional additives, such as flavoring, excipients, stabilizers, effervescent agents, antioxidants, or the like. These additives will be used in conventional amounts, with the exception of excipients, usually be present in total amount of less than about 10 wt.%. For slow release particles, various physiologically acceptable - biologically degradable polymers may be employed, such as polylactates, polyglycolates, polyaldehydes, polyanhydrides, etc.

Any convenient mode of administration may be employed. Administration may be oral, parenteral, topical, etc., such as by injection, oral tablet or powder, or other convenient means. Administration may be daily, multiple dosages per day, bidaily, or other convenient period, depending upon the nature of the administration, whether the cysteine source is administered in a long acting form, or the like. Usually, the amount of cysteine source will be sufficient to raise the thiol level of the blood plasma, when administered in a manner which introduces the cysteine source to the vascular system, at least two µM, desirably to a level of at least about 8 µM, preferably at least about 10 µM, and most preferably to a normal level of from about 15 to 20 µM or possibly higher, e.g., 25 µM. For many drugs, the drug may be administered up to the maximum allowable dosage to provide for counteracting cysteine deficiency. Where oral ingestion is employed, tablets having about 100 mg to 1 g or more of the cysteine source may be used, where the amount of cysteine administered to the patient per day will generally be in the range of about 200 mg to 20 g, or more, preferably about 250 mg to 5 g, more preferably about 1 to 4 g.

The subject cysteine sources may be used in conjunction with other drugs. For example, in the treatment of AIDS, the subject cysteine sources may be employed with various drugs which affect reverse transcriptase. Drugs of interest include analogs of nucleotides, such as AZT, dideoxycytosine, dideoxyinosine, etc.; acyclovir, ribavirin, interferon, ascorbic acid, cytokines, e.g., IL-1, -2, -3 or -4, growth factors, interferons, e.g., γ-, etc. The administered dosage of these drugs will vary, depending upon the disease status of the individual, e.g., fullblown AIDS, the particular drug, the frequency of administration, and the like. Usually, drugs will be administered at a rate of about 5µg to 100 mg/kg/d.

For treatment of AIDS, it may be satisfactory to provide for continuous administration of the cysteine source, while using the anti-viral drugs which have substantial side effects for episodic incidences of viral proliferation. Thus, the cysteine source could be used for maintenance and the antiviral drug for chronic episodes.

It is known to use N-acetyl cysteine for acetaminophen overdose. By providing a combination of acetaminophen at a normal dosage level and a cysteine source, the effect of acetaminophen overdosage may be counteracted and any adverse effect of normal levels of acetaminophen counteracted.

Each of the diseases which may be treated may be associated with a reduced plasma cysteine concentration, and/or a reduced intracellular cysteine/glutathione concentration, and frequently associated with an elevated plasma glutamate concentration.

A cysteine source may also find use with extending the life of stored or administered red blood cells, where the concentrations may be in the range of physiological concentrations.

EXPERIMENTAL

The following examples are offered by way of illustration and not by way of limitation.

In a first study, a number of different components of blood plasma were determined from healthy HIV-infected persons. Amino acids were determined in the blood plasma with a BIOTRONIC LC5001 amino acid analyzer after treatment with sulfosalicylic acid as described in Dröge et al., Biol. Chem. Hoppe-Seyler 369, 143–148(1988).

Peripheral blood mononuclear cells (PBMC) were prepared by mixing 10 ml heparinized blood with 10 ml RPMI 1640 medium. The mixture was layered on top of 5 ml Ficoll and subjected to centrifugation at 1800 rpm for 30 min. The cells at the interface were washed twice with RPMI 1640 medium. Monocytes were prepared by incubating PBMC for 2 h at 37° C. in plastic dishes. Cells were washed with PBS, treated for 30 min., with 0.2 ml 0.5% Triton X-100 (4° C.), and then incubated for another 20 min. at 4° C. with 0.01 ml sulfosalicylic acid (50%). After high speed centrifugation (4° C., 15 min.) the clear supernatant was assayed for glutathione as described in Tietze, Anal. Biochem. 27, 502–522 (1969).

Acid soluble thiol groups were determined in 0.3 ml plasma samples after incubation with 0.015 ml sulfosalicylic acid (50%) for 10 min. at 4° C. and subsequent high speed centrifugation (4° C., 15 min.). Thiol in the supernatant was determined as described in Bannai and Ishii, J. Cell. Physiol. 104, 215–223 (1980), with cysteine as a standard.

Of the subjects in the study, the mean age of males was 28.8 yr, females 25.5 yr, total 27.7 yr.

Some blood samples of these groups contained too few monocytes to allow for useful determination.

The data in the table shows that the acid soluble thiol concentration on the average is about 15 µM in plasma samples from healthy blood donors and 5 µM in the plasma of untreated HIV-infected persons with AIDS or lymphadenopathy syndrome. Some plasma samples analyzed simultaneously for acid soluble thiol and for cysteine revealed that most of the acid soluble thiol is cysteine, but the cysteine assay was not entirely reliable. The subject results are in agreement with earlier studies on healthy human subjects which have shown that mean plasma levels contain about $1-2\times10^{-5}$M cysteine. The decline of the plasma thiol concentration in HIV-infected persons was found to be accompanied by a decrease of the mean intracellular glutathione concentration in PBMC and monocytes. The results in the table also revealed a 3 to 5-fold increase of the mean plasma glutamate level and a reduced plasma methionine level in HIV-infected persons, if compared to a group of healthy blood donors. Some patients have glutamate levels above 180 µM, i.e., 6-fold the normal level. Elevated extracellular glutamate concentrations have been shown to reduce the intracellular cysteine and glutathione concentrations in macrophages and to inhibit their capacity to release cysteine.

TABLE 1

PLASMA AMINO ACID AND THIOL CONCENTRATIONS AND INTRACELLULAR GLUTATHIONE CONCENTRATIONS IN HIV-INFECTED PERSONS AND HEALTHY BLOOD DONORS

| GROUPS | n | plasma glutamate µM/L ± S.E.M. | plasma methionine µM/L ± S.E.M. | plasma cystine plus cysteine µM/L ± S.E.M. | plasma acid soluble thiol µM/L ± S.E.M. | glutathione in PBMC nmoles/mg protein | glutathione in Monocytes nmoles/mg protein |
|---|---|---|---|---|---|---|---|
| A HEALTHY BLOOD DONORS | | | | | | | |
| males | 18 | 33.7 ± 1.7 | 30.6 ± 1.0 | 74.7 ± 2.2 | 15.5 ± 0.9 | 23.6 ± 1.0 | 32.8 ± 1.0 (n = 16) |
| females | 11 | 29.5 ± 1.8 | 29.5 ± 1.3 | 74.7 ± 2.4 | 12.9 ± 1.1 | 25.3 ± 1.2 | 35.0 ± 1.0 (n = 10) |
| total | 29 | 32.1 ± 1.3 | 30.2 ± 0.8 | 74.7 ± 1.6 | 14.5 ± 0.7 | 24.3 ± 0.8 | 33.6 ± 0.7 (n = 26) |
| B UNTREATED HIV+ WITHOUT SYMPTOMS | | | | | | | |
| | 2 | 83.9 ± 12.8 | 20.8 ± 1.2 | 51.9 ± 16.2 | 8.3 ± 1.0 | 21.0 ± 4.4 | 29.6 ± 3.1 |
| C UNTREATED HIV+ WITH LAS | | | | | | | |
| | 18 | 92.1 ± 12.2 | 24.9 ± 1.2 | 68.2 ± 3.7 | 5.3 ± 0.6 | 18.6 ± 0.5 | 24.8 ± 1.1 (n = 14) |
| D UNTREATED HIV+ WITH AIDS/ARC | | | | | | | |
| | 4 | 155.5 ± 20.7 | 21.5 ± 2.5 | 59.8 ± 9.2 | 4.5 ± 0.5 | 18.4 ± 1.3 | 24.3 ± 0.9 |
| E AZT TREATED PERSONS WITH AIDS/ARC | | | | | | | |
| | 17 | 87.6 ± 6.0 | 26.5 ± 1.8 | 65.8 ± 2.8 | 12.6 ± 1.4 | 19.7 ± 0.9 | 26.9 ± 1.8 (n = 13) |
| P-VALUES FOR | | | | WILCOXON RANKTEST | | | |
| A) DIFFERENT C) | | $P < 0.000002$ | $P < 0.0002$ | $P < 0.0002$ | $P < 0.000002$ | $P < 0.00002$ | $P < 0.00003$ |
| A) DIFFERENT D) | | $P < 0.0004$ | $P < 0.005$ | $P < 0.04$ | $P < 0.002$ | $P < 0.04$ | $P < 0.00004$ |
| D) DIFFERENT E) | | $P < 0.003$ | not signif. | not signif. | $P < 0.003$ | not signif. | not signif. |

Patients who had been treated with AZT for various periods between 1 and 12 months showed on the average a substantial recovery of plasma thiol; but glutamate concentrations remained elevated and the intracellular glutathione levels remained low. One patient showed a plasma thiol level of 21 µM after 1 month of AZT treatment. AZT has been previously shown to inhibit HIV replication in vitro and to decrease the mortality if administered to patients with AIDS or AIDS related complex by Fischl et al., N. Engl. J. Med. 317, 185–191 (1987).

Anecdotal results further support the influence of the cysteine source administered to an HIV-infected person as providing for a general improvement in the health status of the individual. Two HIV-1-antibody positive persons were studied. Both persons had a plasma thiol level of 3 µM before treatment. Oral ingestion of multiple 200 mg doses of N-acetyl cysteine was found to raise the thiol level to almost normal values within 1–4 hours; but the plasma thiol level declined again to low levels overnight, i.e., within 10 h after the last dose of N-acetyl cysteine.

Both persons took 5–8 doses of 200 mg N-acetyl cysteine every day for a period of about 4 months. During this 4 month period the $CD8^{30}$ T-cell count increased in both persons by a factor of 4, while the $CD4^+$ T-cell count did not improve markedly. The low $CD4^+$ T-cell count is generally regarded as responsible for the incidence of opportunistic infections in AIDS patients; but there is also the possibility that the remaining T-cells do not work optimally because of the low extracellular cysteine level. At an enhanced cysteine level there is an improved ability of the patient to cope with infections.

The original conditions of the two men were that one of the men had low T-cell counts but otherwise no serious symptoms throughout the period. The other man was in a very critical condition before starting to take the N-acetyl cysteine, among other symptoms, having suffered from a massive weight loss. Within a few weeks his condition improved and his body weight increased rapidly. After starting to take the N-acetyl cysteine, he returned to work after 6 weeks. There was a substantial recovery of physical strength. Over an eight month period the patient has remained able to function and work. Furthermore, there was observed an increase in intracellular glutathione and a decrease in plasma glutamate.

A similar improvement was observed with two additional patients with full blown AIDS, where the patients went from substantial debilitation to being able to function.

It is evident from the above results that a demonstration of an intracellular available cysteine source can result in an enhancement of cysteine intracellularly, concomitantly with glutathione enhancement and serve to substantially reduce debilitating symptoms of diseases such as AIDS. Thus, by providing for a source of cysteine to cells, particularly hematopoietic cells, muscle cells, and cells of the central nervous system, in a form in which the cysteine may be transported to the cytoplasm, suffering and debilitation may be substantially diminished.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for ameliorating the symptoms of a human patient suffering from lymphadenopathy syndrome, AIDS related complex, AIDS, or being seropositive for antibodies for HIV, said method consisting essentially of:

administering to said human HIV seropositive or infected patient N-acetyl cysteine or a pharmacologically acceptable salt thereof, in a physiologically effective amount of at least about 200 mg.

2. A method according to claim 1, wherein a therapeutic amount of an antiviral drug is administered.

3. A method according to claim 2, wherein said antiviral drug is AZT, dideoxycytosine or dideoxyinosine.

* * * * *